United States Patent [19]

Schmidt et al.

[11] 4,333,841
[45] Jun. 8, 1982

[54] DITHIOPHOSPHATE LUBRICANT ADDITIVES

[75] Inventors: Andreas Schmidt, Reinach; Rudolf Kirchmayr, Aesch, both of Switzerland; Donald R. Randell, Stockport, England

[73] Assignee: Ciba-Geigy Corporation, Ardsley, N.Y.

[21] Appl. No.: 184,609

[22] Filed: Sep. 5, 1980

Related U.S. Application Data

[63] Continuation of Ser. No. 952,920, Oct. 19, 1978, abandoned, which is a continuation of Ser. No. 862,078, Dec. 19, 1977, abandoned.

[51] Int. Cl.$^3$ .................. C10M 71/46; C07F 9/32
[52] U.S. Cl. ............... 252/32.7 E; 252/46.7; 260/936; 260/941; 260/943
[58] Field of Search ................... 252/32.7 E

[56] References Cited

U.S. PATENT DOCUMENTS

| | | | |
|---|---|---|---|
| 2,494,283 | 1/1950 | Cassaday et al. | 260/943 |
| 2,645,657 | 7/1953 | Rudel et al. | 260/941 |
| 2,959,610 | 11/1960 | Young et al. | 260/941 |
| 3,013,940 | 12/1961 | Fusco et al. | 260/943 |
| 3,102,020 | 8/1963 | Spezials et al. | 260/943 |
| 3,106,510 | 8/1963 | Szabo et al. | 260/943 |
| 3,134,801 | 5/1964 | Sehring et al. | 260/941 |
| 3,658,800 | 4/1972 | Beriger | 260/347.1 |
| 3,755,313 | 8/1973 | Beriger | 260/243 B |
| 3,807,984 | 4/1974 | Beriger | 71/87 |
| 3,833,600 | 9/1974 | Toepfl | 71/87 |
| 3,941,808 | 3/1976 | Pratt . | |
| 3,942,971 | 3/1976 | Toepfl . | |

FOREIGN PATENT DOCUMENTS

| | | |
|---|---|---|
| 859735 | 1/1961 | United Kingdom . |
| 1255946 | 12/1971 | United Kingdom . |
| 209457 | 3/1968 | U.S.S.R. . |
| 295791 | 8/1971 | U.S.S.R. . |

OTHER PUBLICATIONS

Berkelhammer et al., J. Org. Chem. 26, 2281, (1961).

*Primary Examiner*—Anton H. Sutto
*Attorney, Agent, or Firm*—Luther A. R. Hall

[57] ABSTRACT

Dithiophosphate lubricant additives of the formula I

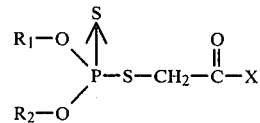

wherein
$R_1$ and $R_2$, each independently of the other, represents $C_3$–$C_{12}$alkyl which can be interrupted by 1 to 2 oxygen atoms, $C_6$–$C_{10}$aryl or ($C_1$–$C_{12}$alkyl)-aryl, or $R_1$ and $R_2$ together represent $C_2$–$C_{12}$alkylene which can be interrupted by 1 or 2 oxygen atoms, and represents —OH, —NR$_3$R$_4$, —OH.NR$_3$R$_4$R$_5$, —NHCH$_2$COOH, —NHCH$_2$COOR$_1$, —NH(CH$_2$COOH)$_2$, —N(CH$_2$COOR$_1$)$_2$, —N(CH$_2$COOH)$_2$.NR$_3$R$_4$R$_5$, —N(CH$_2$COOH.NR$_3$R$_4$R$_5$)$_2$, —NHCH$_2$OH or —N(CH$_2$CH$_2$OH)$_2$, wherein $R_3$, $R_4$ and $R_5$, each independently of the other, represents hydrogen or $C_1$–$C_{18}$alkyl, or $R_3$ and $R_4$ together represent $C_3$–$C_{12}$alkylene which can be interrupted by an oxygen, sulphur or nitrogen atom.

4 Claims, No Drawings

DITHIOPHOSPHATE LUBRICANT ADDITIVES

This is a continuation of application Ser. No. 952,920, filed on Oct. 19, 1978, now abandoned, which in turn is a continuation of application Ser. No. 862,078, filed on Dec. 19, 1977, now abandoned.

The present invention relates to dithiophosphate derivatives, to their use as lubricant additives, and to the lubricating oil formulations which contain the novel compounds.

Various additives are usually added to mineral and synthetic lubricants to improve their performance properties. In particular there is a need for additives which will protect the devices to be lubricated from frictional wear. The requirement made of such wear inhibitors is that they shall increase the load bearing capacity of the lubricant and not have a corrosive action on the metal parts to be protected. From Russian Pat. No. 295,791 it is known to use N-monosubstituted dithiophosphate acetamide lubricating oil additives, and N-disubstituted dithiophosphate acetamides are known as pesticides from British Patent Specification No. 1,255,946.

The surprising invention has now been made that the dithiophosphates of the formula I are superior to the known high pressure lubricant additives, especially in respect of freedom from ashes, thermostability, non-corrosiveness to iron and nonferrous metals, and resistance to hydrolysis.

Accordingly, the invention provides dithiophosphate lubricant additives of the formula I

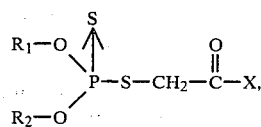

wherein
$R_1$ and $R_2$, each independently of the other, represents $C_3-C_{12}$-alkyl which can be interrupted by 1 or 2 oxygen atoms, $C_6-C_{10}$aryl or $(C_1-C_{12}alkyl)$-aryl, or $R_1$ and $R_2$ together represent $C_2-C_{12}$alkylene which can be interrupted by 1 or 2 oxygen atoms, and
X represents —OH, —NR$_3$R$_4$, —OH.NR$_3$R$_4$R$_5$, —NHCH$_2$COOH, —NHCH$_2$COOR$_1$, —N(CH$_2$COOH)$_2$, —N(CH$_2$COOR$_1$)$_2$, —N(CH$_2$COOH)$_2$.NR$_3$R$_4$R$_5$, —N(CH$_2$COOH.NR$_3$R$_4$R$_5$)$_2$, —NHCH$_2$OH or —N(CH$_2$CH$_2$OH)$_2$, wherein $R_3$, $R_4$ and $R_5$, each independently of the other, represents hydrogen or $C_1-C_{18}$alkyl, or $R_3$ and $R_4$ together represent $C_3-C_{12}$alkylene which can be interrupted by an oxygen, sulphur or nitrogen.

Alkyl represented by $R_1$ and $R_2$ is straight-chain or branched alkyl of 3 to 12 carbon atoms, such as n-propyl, isopropyl, n-butyl, isobutyl, sec-butyl, amyl, neopentyl, hexyl, 1-methylpentyl, n-octyl, isooctyl, tert-octyl, 2-ethylhexyl, n-decyl, 2-ethyldecyl and n-dodecyl.

Alkyl represented by $R_1$ and $R_2$ which contains 1 or 2 oxygen atoms in the chain is straight-chain or branched alkyl of 3 to 12 carbon atoms, in particular alkoxyalkyl having a total of 3 to 12 carbon atoms, for example 2-methoxyethyl, 2-ethoxyethyl, 2-n-propoxyethyl, 2-isopropoxyethyl, 2-n-butoxyethyl and 2-n-octoxyethyl.

Alkylene of 2 to 12 carbon atoms represented by $R_1$ and $R_2$ is straight-chain or branched alkylene, in particular ethylene or propylene-1,3 which can be mono- or polysubstituted by $C_1-C_4$alkyl, in particular mono- or polymethylated propylene-1,3, such as ethylene, propylene-1,3, butylene-1,4,2-methylpropylene-1,3, 2,2-dimethylpropylene-1,3 and 1,1,3-trimethylpropylene-1,3.

Aryl represented by $R_1$ and $R_2$ is in particular phenyl, alkylaryl, preferably phenyl which is di-, tri- or, especially, monosubstituted by $C_1-C_{12}$alkyl, preferably $C_1-C_4$alkylated phenyl, such as methylphenyl or isopropylphenyl.

Alkyl represented by $R_3$, $R_4$ and $R_5$ is, in addition to the values given for $R_1$, also methyl or ethyl or $C_{13}-C_{18}$alkyl, such as n-octadecyl.

$C_3-C_{12}$alkylene represented by $R_3$ and $R_4$ together is in particular optionally mono- or polyalkylated, such as $C_1-C_4$alkylated, especially methylated, butylene-1,4 or pentylene-1,5, such as in particular butylene-1,4 or pentylene-1,5 itself. If such an alkylene radical is interrupted by an oxygen, sulphur or nitrogen atom, it is, together with the nitrogen atom to which $R_3$ and $R_4$ are attached, morpholino, thiomorpholino, piperazino or 4-methylpiperazino.

Particularly suitable dithiophosphates are those of the formula I in which $R_1$ has the same meaning as $R_2$ and represents $C_3-C_8$alkyl, or $R_1$ and $R_2$ together represent $C_2-C_8$alkylene, and X represents —NR$_3$R$_4$, —OH or —OH.NR$_3$R$_4$R$_5$, wherein each of $R_3$, $R_4$ and $R_5$ independently represents hydrogen or $C_1-C_{18}$alkyl.

Preferred dithiophosphates are in particular those of the formula I in which $R_1$ has the same meaning as $R_2$ and represents $C_3-C_8$alkyl, or $R_1$ and $R_2$ together represent $C_2-C_8$alkylene, X represents —NR$_3$R$_4$, and $R_3$ has the same meaning as $R_4$ and represents $C_1-C_{18}$alkyl.

The most preferred dithiophosphates are those named in the Examples.

The novel compounds of the formula I are obtained by methods which are known per se, either according to the process of British Patent Specification No. 1,255,946 to give compounds of the formula I in which X is —NR$_3$R$_4$, or by reacting an acid $(R_1O)(R_2O)P(S)$—S—CH$_2$—COOH with an amine NR$_3$R$_4$R$_5$ to give compounds of the formula I in which X is —OH.NR$_3$R$_4$R$_5$. However, it is also possible to react a dithiophosphoric acid ester with a correspondingly substituted chloroacetamide, such as with the disodium salt of N,N-bis-carboxymethylchloroacetamide.

The compounds of the formula I, even when used in very small amounts, act as high-pressure additives in lubricants. Accordingly, mineral and synthetic lubricating oils, as well as mixtures thereof, which contain 0.001 to 5 percent by weight, based on the lubricant, and preferably 0.02 to 3 percent by weight, of a compound of the formula I, exhibit excellent highpressure lubricating properties which become evident due to the greatly reduced signs of wear of the friction surfaces to be lubricated. The suitable lubricants are known to the skilled person and are described for example in the "Schmiermittel Taschenbuch" (Hüthig Verlag, Heidelberg, 1974).

The lubricating oil formulation can contain still further additives which are added to improve certain performance properties, such as antioxidants, metal deactivators, rust inhibitors, viscosity index improvers, pour-point depressors, dispersants/detergents and other wear resisting additives.

Examples of antioxidants are:

(a) Alkylated and non-alkylated aromatic amines and mixtures thereof, for example: dioctyldiphenylamine, mono-tert-octylphenyl-α- and -β-naphthylamines, phenotriazine, dioctylphenothiazine, phenyl-α-naphthylamine, N,N'-disec-butyl-p-phenylenediamine.

(b) Sterically hindered phenols, for example: 2,6-di-tert-butyl-p-cresol, 4,4'-bis-(2,6-diisopropylphenol), 2,4,6-triisopropylphenol, 2,2'-thio-bis-(4-methyl-6-tert-butylphenol), 4,4'-methylene-bis-(2,6-di-tert-butylphenol).

(c) Alkyl-, aryl- or aralkylaryl-phosphites, for example: trinonylphosphite, triphenylphosphite, diphenyldecylphosphite.

(d) Esters of thiodipropionic acid or thiodiacetic acid, for example: dilaurylthiodipropionate or dioctylthiodiacetate.

(e) Salts of carbamic and dithiophosphoric acids, for example: antimony diamyldithiocarbamate, zinc diamyldithiophosphate.

(f) A combination of two or more of the above antioxidants, for example: an alkylated amine and a sterically hindered phenol.

Examples of metal deactivators are:

(a) for copper, for example benzotriazole, tetrahydrobenzotriazole, 2-mercaptobenzotriazole, 2,5-dimercaptothiadiazole, salicylidene propylenediamine, salts of salicylaminoguanidine.

(b) for lead, for example sebacid acid derivatives, quinizarine, propyl gallate.

(c) A combination of two or more of the above additives.

Examples of rust inhibitors are:

(a) Organic acids, the esters, metal salts and anhydrides thereof, for example: N-oleyl-sarcosine, sorbitan mono-oleate, lead naphthenate, dodecenylsuccinic anhydride.

(b) Nitrogenous compounds, for example:
I. Primary, secondary or tertiary aliphatic or cycloaliphatic amines and amine salts of organic and inorganic acids, for example oil-soluble alkylammonium carboxylates.
II. Heterocyclic compounds, for example substituted imidazolines and oxazolines.

(c) Phosphorus-containing compounds, for example: amine salts of phosphoric acid partial esters.

(d) Sulphur-containing compounds, for example: barium dinonylnaphthalenesulphonates, calcium petroleum sulphonates.

(e) Combinations of two or more of the above additives.

Examples of viscosity index improvers are:

polymethylacrylates, vinyl pyrrolidone/methacrylate copolymers, polybutene, olefin copolymers, styrene/acrylate copolymers.

Examples of pour-point depressors are:

polymethacrylates, alkylated naphthalene derivatives.

Examples of dispersants/detergents are:

polybutenylsuccinic imides, polybutenylphosphonic acid derivatives, superbasic magnesium, calcium and barium sulphonates and phenolates.

Examples of other wear resisting additives are:

compounds which contain sulphur and/or phosphorus and/or halogen, such as sulphurised vegetable oils, zinc dialkyldithiophosphates, tritolylphosphate, chlorinated paraffins, alkyl- and aryldisulphides.

The invention is illustrated by the following Examples.

EXAMPLE 1

$$\left(\begin{array}{c}CH_3\\ \diagdown\\ \diagup\\ CH_3\end{array}CHO\right)_2 \overset{S}{\underset{\|}{P}}-SCH_2\overset{O}{\underset{\|}{C}}-N\left(-CH\begin{array}{c}CH_3\\ \diagup\\ \diagdown\\ CH_3\end{array}\right)_2$$

83.2 g (0.33 mole) of the potassium salt of O,O-diisopropyl-dithiophosphoric acid are suspended in 200 ml of acetone and, with stirring, the suspension is treated with a solution of 53.3 g (0.3 mole) of chloroacetic N,N-diisopropylamide in 200 ml of acetone. The reaction mixture is then stirred for 12 hours at room temperature. Precipitated potassium chloride is filtered off and the filtrate is completely concentrated and the oily residue is taken up in toluene. After washing three times with water, the organic phase is concentrated to dryness under reduced pressure, affording O,O-diisopropyl-S-(N,N-diisopropyl-carboxamidomethyl)-dithiophosphate with a melting point of about 30° C. (Additive 1).

The corresponding O,O-dialkyl-S-(N,N-dialkylcarboxamidomethyl)-dithiophosphates are obtained by repeating the above procedure, but substituting the homologues listed in Table 1 for O,O-diisopropyl-dithiophosphoric acid or chloroacetic-N,N-diisopropylamide or both:

TABLE 1

| Additive | Potassium salt | Chloroacetamide | m.p. | Thionophosphate |
|---|---|---|---|---|
| 2 | $\left(\begin{array}{c}CH_3\\ \diagdown\\ \diagup\\ CH_3\end{array}CHO\right)_2 \overset{S}{\underset{\|}{P}}SK$ | $ClCH_2\overset{O}{\overset{\|}{C}}\diagdown N\left(\begin{array}{c}CH_3\\ \diagup\\ CH_2CH\\ \diagdown\\ CH_3\end{array}\right)_2$ | oil | 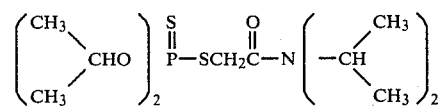 |

TABLE 1-continued

| Additive | Potassium salt | Chloroacetamide | m.p. | Thionophosphate |
|---|---|---|---|---|
| 3 | $\left(\begin{array}{c}CH_3\\ \phantom{x}\\ CH_3\end{array}CHO\right)_2 \overset{S}{\underset{\|}{P}}SK$ | $ClCH_2\overset{O}{\underset{\|}{C}}N(CH_2CH_2CH_3)_2$ | oil | $\left(\begin{array}{c}CH_3\\ \phantom{x}\\ CH_3\end{array}CHO\right)_2 \overset{S}{\underset{\|}{P}}SCH_2CON(CH_2CH_2CH_3)_2$ |
| 4 | $\left(\begin{array}{c}CH_3\\ \phantom{x}\\ CH_3\end{array}CHO\right)_2 \overset{S}{\underset{\|}{P}}SK$ | $ClCH_2\overset{O}{\underset{\|}{C}}N(C_4H_9n)_2$ | oil | $\left(\begin{array}{c}CH_3\\ \phantom{x}\\ CH_3\end{array}CHO\right)_2 \overset{S}{\underset{\|}{P}}SCH_2CON(C_2H_{2n})_2$ |
| 5 | $(CH_3CH_2CH_2O)_2\overset{S}{\underset{\|}{P}}SK$ | $ClCH_2\overset{O}{\underset{\|}{C}}-N\begin{pmatrix}\\ \\ CH_3\end{pmatrix}$ | oil | $(CH_3CH_2CH_2O)_2\overset{S}{\underset{\|}{P}}SCH_2CON\begin{pmatrix}\\ \\ CH_3\end{pmatrix}$ |
| 6 | $\left(\begin{array}{c}CH_3\\ \phantom{x}\\ CH_3\end{array}CHCH_2O\right)_2 \overset{S}{\underset{\|}{P}}SK$ | $ClCH_2\overset{O}{\underset{\|}{C}}-N\left(CH_2CH\begin{array}{c}CH_3\\ \\ CH_3\end{array}\right)_2$ | oil | $\left(\begin{array}{c}CH_3\\ \phantom{x}\\ CH_3\end{array}CHCH_2O\right)_2 \overset{S}{\underset{\|}{P}}SCH_2CON\left(CH_2CH\begin{array}{c}CH_3\\ \\ CH_3\end{array}\right)_2$ |
| 7 | $\left(\begin{array}{c}CH_3\\ \phantom{x}\\ CH_3\end{array}CHCH_2O\right)_2 \overset{S}{\underset{\|}{P}}SK$ | $ClCH_2\overset{O}{\underset{\|}{C}}N\left(CH\begin{array}{c}CH_3\\ \\ CH_3\end{array}\right)_2$ | oil | $\left(\begin{array}{c}CH_3\\ \phantom{x}\\ CH_3\end{array}CHCH_2O\right)_2 \overset{S}{\underset{\|}{P}}SCH_2CON\left(CH\begin{array}{c}CH_3\\ \\ CH_3\end{array}\right)_2$ |
| 8 | $\left(\begin{array}{c}CH_3\\ \phantom{x}\\ CH_3\end{array}CHCH_2O\right)_2 \overset{S}{\underset{\|}{P}}SK$ | $ClCH_2\overset{O}{\underset{\|}{C}}N(CH_2CH_2CH_3)_2$ | oil | $\left(\begin{array}{c}CH_3\\ \phantom{x}\\ CH_3\end{array}CHCH_2O\right)_2 \overset{S}{\underset{\|}{P}}SCH_2CON(CH_2CH_2CH_3)_2$ |
| 9 | $\left(\begin{array}{c}CH_3\\ \phantom{x}\\ CH_3\end{array}CHCH_2O\right)_2 \overset{S}{\underset{\|}{P}}SK$ | $ClCH_2\overset{O}{\underset{\|}{C}}N(C_4H_9n)_2$ | oil | $\left(\begin{array}{c}CH_3\\ \phantom{x}\\ CH_3\end{array}CHCH_2O\right)_2 \overset{S}{\underset{\|}{P}}SCH_2CON(C_4H_9n)_2$ |
| 10 | $(nC_4H_9O)_2\overset{S}{\underset{\|}{P}}SK$ | $ClCH_2\overset{O}{\underset{\|}{C}}N\left(CH_2CH\begin{array}{c}CH_3\\ \\ CH_3\end{array}\right)_2$ | oil | $(nC_4H_9O)_2\overset{S}{\underset{\|}{P}}SCH_2CON\left(CH_2CH\begin{array}{c}CH_3\\ \\ CH_3\end{array}\right)_2$ |
| 11 | $(nC_4H_9O)_2\overset{S}{\underset{\|}{P}}SK$ | $ClCH_2\overset{O}{\underset{\|}{C}}N\left(CH\begin{array}{c}CH_3\\ \\ CH_3\end{array}\right)_2$ | oil | $(nC_4H_9O)_2\overset{S}{\underset{\|}{P}}SCH_2CON\left(CH\begin{array}{c}CH_3\\ \\ CH_3\end{array}\right)_2$ |
| 12 | $(nC_4H_9O)_2\overset{S}{\underset{\|}{P}}SK$ | $ClCH_2\overset{O}{\underset{\|}{C}}N(C_8H_{17}n)_2$ | oil | $(nC_4H_9O)_2\overset{S}{\underset{\|}{P}}SCH_2CON(C_8H_{17}n)_2$ |
| 13 | $\begin{array}{c}CH_3\\ CH_3-C-O\\ \phantom{xx}\vert\phantom{xx}\\ \phantom{xxx}CH_2\\ CH_3-CH-O\end{array}\overset{S}{\underset{\|}{P}}SK$ | $ClCH_2\overset{O}{\underset{\|}{C}}N(CH_2CH_2CH_3)_2$ | oil | $\begin{array}{c}CH_3\\ CH_3-C-O\\ \phantom{xx}\vert\phantom{xx}\\ \phantom{xxx}CH_2\\ CH_3-CH-O\end{array}\overset{S}{\underset{\|}{P}}SCH_2CON(CH_2CH_2CH_3)_2$ |
| 14 | $\begin{array}{c}CH_3\\ CH_3-C-O\\ \phantom{xx}\vert\phantom{xx}\\ \phantom{xxx}CH_2\\ CH_3-CH-O\end{array}\overset{S}{\underset{\|}{P}}SK$ | $ClCH_2\overset{O}{\underset{\|}{C}}N(C_4H_9n)_2$ | oil | $\begin{array}{c}CH_3\\ CH_3-C-O\\ \phantom{xx}\vert\phantom{xx}\\ \phantom{xxx}CH_2\\ CH_3-CH-O\end{array}\overset{S}{\underset{\|}{P}}SCH_2CON(C_4H_9n)_2$ |
| 15 | $\begin{array}{c}CH_3\\ CH_3-C-O\\ \phantom{xx}\vert\phantom{xx}\\ \phantom{xxx}CH_2\\ CH_3-CH-O\end{array}\overset{S}{\underset{\|}{P}}SK$ | $ClCH_2\overset{O}{\underset{\|}{C}}N\left(CH_2CH\begin{array}{c}CH_3\\ \\ CH_3\end{array}\right)_2$ | oil | $\begin{array}{c}CH_3\\ CH_3-C-O\\ \phantom{xx}\vert\phantom{xx}\\ \phantom{xxx}CH_2\\ CH_3-CH-O\end{array}\overset{S}{\underset{\|}{P}}SCH_2CON\left(CH_2CH\begin{array}{c}CH_3\\ \\ CH_3\end{array}\right)_2$ |
| 16 | $\begin{array}{c}CH_3\\ CH_3-C-O\\ \phantom{xx}\vert\phantom{xx}\\ \phantom{xxx}CH_2\\ CH_3-CH-O\end{array}\overset{S}{\underset{\|}{P}}SK$ | $ClCH_2\overset{O}{\underset{\|}{C}}N\left(CH\begin{array}{c}CH_3\\ \\ CH_3\end{array}\right)_2$ | 70° C. | $\begin{array}{c}CH_3\\ CH_3-C-O\\ \phantom{xx}\vert\phantom{xx}\\ \phantom{xxx}CH_2\\ CH_3-CH-O\end{array}\overset{S}{\underset{\|}{P}}SCH_2CON\left(CH\begin{array}{c}CH_3\\ \\ CH_3\end{array}\right)_2$ |

TABLE 1-continued

| Additive | Potassium salt | Chloroacetamide | m.p. | Thionophosphate |
|---|---|---|---|---|
| 17 | $\begin{array}{c}CH_3\\|\\CH_3-C-O\\|\quad\quad\quad\backslash\\CH_2\quad\quad S\\|\quad\quad\quad\|\\CH_3-CH-O\quad PSK\end{array}$ | $ClCH_2\overset{O}{\overset{\|}{C}}N(C_8H_{17}n)_2$ | oil | $\begin{array}{c}CH_3\\|\\CH_3-C-O\\|\quad\quad\quad\backslash\\CH_2\quad\quad\quad PSCH_2CON(C_8H_{17}n)_2\\|\quad\quad\quad/\\CH_3-CH-O\end{array}$ |
| 18 | $\begin{array}{c}CH_3\quad CH_2-O\quad S\\ \backslash\,/\quad\quad\quad\quad\backslash\|\\ C\quad\quad\quad\quad\quad PSK\\ /\quad\backslash\quad\quad\quad/\\ CH_3\quad CH_2-O\end{array}$ | $ClCH_2\overset{O}{\overset{\|}{C}}N(C_8H_{17}n)_2$ | oil | $\begin{array}{c}CH_3\quad CH_2-O\quad S\\ \backslash\,/\quad\quad\quad\quad\backslash\|\\ C\quad\quad\quad\quad\quad PSCH_2CON(C_8H_{17}n)_2\\ /\quad\backslash\quad\quad\quad/\\ CH_3\quad CH_2-O\end{array}$ |
| 19 | $(iC_8H_{17}O)_2\overset{S}{\overset{\|}{P}}SK$ | $ClCH_2\overset{O}{\overset{\|}{C}}N(CH_2CH_2CH_3)_2$ | oil | $(iC_8H_{17}O)_2\overset{S}{\overset{\|}{P}}SCH_2CON(CH_2CH_2CH_3)_2$ |
| 20 | $(iC_8H_{17}O)_2\overset{S}{\overset{\|}{P}}SK$ | $ClCH_2\overset{O}{\overset{\|}{C}}N(C_4H_9n)_2$ | oil | $(iC_8H_{17}O)_2\overset{S}{\overset{\|}{P}}SCH_2CON(C_4H_9n)_2$ |
| 21 | $(iC_8H_{17}O)_2\overset{S}{\overset{\|}{P}}SK$ | $ClCH_2\overset{O}{\overset{\|}{C}}N\left(CH\diagup_{\diagdown CH_3}^{CH_3}\right)_2$ | oil | $(iC_8H_{17}O)_2\overset{S}{\overset{\|}{P}}SCH_2CON\left(CH\diagup_{\diagdown CH_3}^{CH_3}\right)_2$ |
| 22 | $(C_9H_{19}-\!\!\langle\bigcirc\rangle\!\!-O)\overset{S}{\overset{\|}{P}}SK$ | $ClCH_2\overset{O}{\overset{\|}{C}}N\left(CH\diagup_{\diagdown CH_3}^{CH_3}\right)_2$ | oil | $(C_9H_{19}-\!\!\langle\bigcirc\rangle\!\!-O)_2\overset{S}{\overset{\|}{P}}SCH_2\overset{O}{\overset{\|}{C}}N(C_3H_7(i))_2$ |
| 23 | " | $ClCH_2\overset{O}{\overset{\|}{C}}N\left(CH_2CH\diagup_{\diagdown CH_3}^{CH_3}\right)_2$ | oil | $(C_9H_{19}-\!\!\langle\bigcirc\rangle\!\!-O)_2\overset{S}{\overset{\|}{P}}SCH_2\overset{O}{\overset{\|}{C}}N(C_4H_9(i))_2$ |

EXAMPLE 2

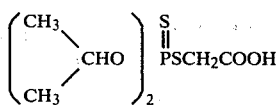

80 g (0.31 mole) of the potassium salt of O,O-diisopropyl-dithiophosphoric acid are dissolved in water and the solution is treated, with stirring, with a solution of 36.1 g (0.31 mole) of the sodium salt of chloroacetic acid in 10 ml of water. The reaction mixture is stirred for 10 hours at room temperature, then acidified with 50 ml of 6 N hydrochloric acid and subsequently extracted with 200 ml of toluene. The toluene phase is washed twice with water and then completely concentrated under reduced pressure, affording O,O-diisopropyl-S-carboxymethyl-dithiophosphate as a light yellow oil.

The corresponding S-carboxymethyl-dithiophosphates are obtained as light yellow oils by repeating the above procedure, but substituting the potassium salt of O,O-diisobutyl-, O,O-di-n-butyl- or O,O-diisooctyl- dithiophosphoric acid for the potassium salt of O,O-diisopropyl-dithiophosphoric acid. O,O-diisooctyl-S-carboxymethyl-dithiophosphate is additive 42.

EXAMPLE 3

5.12 g (0.02 mole) of O,O-diisopropyl-S-carboxymethyl-dithiophosphate are dissolved in 50 ml of toluene and the solution is treated, with stirring, with 3.8 g (0.02 mole) of Primene 81R (mixture of primary $C_{12}$–$C_{15}$tertalkylamines, Röhm and Haas, U.S.A.). The solvent is completely distilled off under reduced pressure, yielding a yellowish transparent oil which is readily soluble in hexane or mineral oil. (Additive 24).

The corresponding ammonium salts are obtained by repeating the above procedure, but substituting the homologues listed in Table 2 for O,O-diisopropyl-S-carboxymethyl-dithiosphophate or Primene 81R or both:

TABLE 2

| Additive | Carboxylic acid | Amine | m.p. | Ammonium salt |
|---|---|---|---|---|
| 25 | $\left(\begin{array}{c}CH_3\\ \backslash\\ \quad\quad CHO\\ /\\ CH_3\end{array}\right)_2\overset{S}{\overset{\|}{P}}SCH_2COOH$ | $nC_4H_9NH_2$ | oil | $\left(\begin{array}{c}CH_3\\ \backslash\\ \quad\quad CHO\\ /\\ CH_3\end{array}\right)_2\overset{S}{\overset{\|}{P}}SCH_2COOH\,.$ $H_2NC_4H_9n$ |

TABLE 2-continued

| Additive | Carboxylic acid | Amine | m.p. | Ammonium salt |
|---|---|---|---|---|
| 26 | $\left[\begin{array}{c}CH_3\\CH_3\end{array}CHO\right]_2 \overset{S}{\underset{\|}{P}}SCH_2COOH$ | $\left(\begin{array}{c}CH_3\\CH_3\end{array}CH\right)_2 NH$ | 90° C. | $\left[\begin{array}{c}CH_3\\CH_3\end{array}CHO\right]_2 \overset{S}{\underset{\|}{P}}SCH_2COOH \cdot NH\left[\begin{array}{c}CH_3\\CH\\CH_3\end{array}\right]_2$ |
| 27 | $\left[\begin{array}{c}CH_3\\CH_3\end{array}CHO\right]_2 \overset{S}{\underset{\|}{P}}SCH_2COOH$ | $(i)C_8H_{17}NH_2$ | oil | $\left[\begin{array}{c}CH_3\\CH_3\end{array}CHO\right]_2 \overset{S}{\underset{\|}{P}}SCH_2COOH \cdot H_2NC_8H_{17}(i)$ |
| 28 | $\left[\begin{array}{c}CH_3\\CH_3\end{array}CHO\right]_2 \overset{S}{\underset{\|}{P}}SCH_2COOH$ | $(t)C_{18}-C_{20}H_{37}-H_{41}NH_2$ (Primene JM-T) | oil | $\left[\begin{array}{c}CH_3\\CH_3\end{array}CHO\right]_2 \overset{S}{\underset{\|}{P}}SCH_2COOH \cdot H_2NC_{18}H_{37}(t)$ (Primene JM-T) |
| 29 | $(nC_4H_9O)_2\overset{S}{\underset{\|}{P}}SCH_2COOH$ | $(t)C_{12}H_{25}NH_2$ (Primene 81-R) | oil | $(nC_4H_9O)_2\overset{S}{\underset{\|}{P}}SCH_2COOH \cdot H_2NC_{12}H_{25}(t)$ (Primene (81-R) |
| 30 | $\left[\begin{array}{c}CH_3\\CH_3\end{array}CHCH_2O\right]_2 \overset{S}{\underset{\|}{P}}SCH_2COOH$ | $\left(\begin{array}{c}CH_3\\CH_3\end{array}CH\right)_2 NH$ | oil | $\left[\begin{array}{c}CH_3\\CH_3\end{array}CH-CH_2O\right]_2 \overset{S}{\underset{\|}{P}}SCH_2COOH \cdot HN\left[\begin{array}{c}CH_3\\CH\\CH_3\end{array}\right]_2$ |
| 31 | $\left[\begin{array}{c}CH_3\\CH_3\end{array}CHCH_2O\right]_2 \overset{S}{\underset{\|}{P}}SCH_2COOH$ | $(n)C_4H_9NH_2$ | oil | $\left[\begin{array}{c}CH_3\\CH_3\end{array}CHCH_2O\right]_2 \overset{S}{\underset{\|}{P}}SCH_2COOH \cdot H_2NC_4H_9(n)$ |
| 32 | $(iC_8H_{17}O)_2\overset{S}{\underset{\|}{P}}SCH_2COOH$ | $(n)C_4H_9NH_2$ | oil | $(iC_8H_{17}O)_2\overset{S}{\underset{\|}{P}}SCH_2COOH \cdot H_2NC_4H_9(n)$ |
| 33 | $(iC_8H_{17}O)_2\overset{S}{\underset{\|}{P}}SCH_2COOH$ | $HN\left[\begin{array}{c}CH_3\\CH\\CH_3\end{array}\right]_2$ | oil | $(iC_8H_{17}O)_2\overset{S}{\underset{\|}{P}}SCH_2COOH \cdot HN\left[\begin{array}{c}CH_3\\CH\\CH_3\end{array}\right]_2$ |
| 34 | $(iC_8H_{17}O)_2\overset{S}{\underset{\|}{P}}SCH_2COOH$ | $H_2NC_{12}H_{25}(t)$ (Primene 81-R) | oil | $(iC_8H_{17}O)_2\overset{S}{\underset{\|}{P}}SCH_2COOH \cdot H_2NC_{12}H_{25}(t)$ Primene 81-R |
| 35 | " | $H_2NC_8H_{17}(i)$ | oil | $(iC_8H_{17}O)_2\overset{S}{\underset{\|}{P}}SCH_2COOH \cdot H_2NC_8H_{17}(i)$ Primene 81-R |
| 36 | " | $HN(C_8H_{17}i)_2$ | oil | $(iC_8H_{17}O)_2\overset{S}{\underset{\|}{P}}SCH_2COOH \cdot HN(C_8H_{17}i)_2$ Primene 81-R |
| 37 | " | $HN(C_4H_9)_2$ | oil | $(iC_8H_{17}O)_2\overset{S}{\underset{\|}{P}}SCH_2COOH \cdot HN(C_4H_9)_2$ Primene 81-R |

EXAMPLE 4

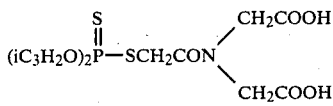

25.4 g (0.1 mole) of the disodium salt of N,N-bis-carboxymethyl-chloroacetamide are charged into 100 ml of dimethyl acetamide together with 4 g (0.1 mole) of sodium hydroxide. Then 21.4 g (0.1 mole) of dithiophosphoric acid O,O-diisopropyl ester are added dropwise and the reaction mixture is stirred for 12 hours at room temperature. Then 17 ml of hydrochloric acid are added and the reaction mixture is poured into 1500 ml of water. After extraction with chloroform, the organic phase is completely concentrated, yielding O,O-diisopropyl-S-[(N,N-bis-carboxymethyl)-carbamoylmethyl]-dithiophosphoric acid ester as a yellowish oil.

EXAMPLE 5

The procedure of Example 4 is repeated, substituting an equimolar amount of dithiophosphoric acid O,O-diisooctyl ester for dithiophosphoric acid O,O-diisopropyl ester, to give the isooctyl homologue also as a yellowish oil. (Additive 30).

EXAMPLE 6

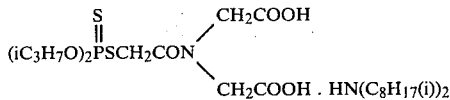

15.5 g (0.04 mole) of O,O-diisopropyl-S-[(N,N-bis-carboxymethyl)-carbamoyl]-dithiophosphoric acid ester are dissolved in 100 ml of toluene and the solution is treated with 9.7 g (0.04 mole) of diisooctylamine. The solvent is completely distilled off under reduced pressure, yielding a reddish yellow oil which is readily soluble in hexane or mineral oil. (Additive 39).

EXAMPLE 7

The procedure of Example 6 is repeated, substituting an equimolar amount of the corresponding diisopropyl ester for the O,O-diisopropyl ester and an equimolar amount of Primene 81-R (vide Example 3) for the diisooctylamine, to give the corresponding ammonium salt as a yellowish oil. (Additive 40).

EXAMPLE 8

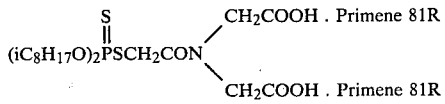

The diammonium salt is obtained by doubling the amount of Primene 81-R in Example 7 and repeating the same procedure. (Additive 41).

EXAMPLE 9

The exceptional load bearing properties of the lubricant additives are also observed in the test on the gearwheel deformation test stand of the "Forschungsstelle für Zahnräder und Getriebe" (FZG).

To this end, mixtures of the additives of the present invention were prepared in a non-doped mineral lubricating oil (viscosity: 20 cS/50° C.) and tested with the FZG machine in accordance with DIN 51354 (normal test A/8.3/90). For comparison, non-doped lubricating oil without addition of the additives was also tested.

The results of these experiments are reported in Table 3.

TABLE 3

| Test | Additive | Concentration in % by weight | Ams (mg/KWh) | Failure load stage |
|---|---|---|---|---|
| 1 | no | — | 0.61 | 6–7 |
| 2 | 1 | 0.5 | 0.1 | 12 |
| 3 | 5 | 0.5 | 0.2 | 10–11 |
| 4 | 5 | 1 | 0.18 | 11–12 |
| 5 | 14 | 0.1 | 0.175 | 9–10 |
| 6 | 14 | 0.175 | 0.12 | 11 |
| 7 | 14 | 0.25 | 0.1 | 12 |
| 8 | 24 | 0.5 | — | >12 |
| 9 | 33 | 0.5 | — | >12 |

EXAMPLE 10

The following values were determined with a Shell four ball tester for lubricating oils: (Tentative Method IP 239/69, extreme pressure and wear lubricant test for oils and greases, four-ball machine).

(1) I.S.L.: initial seizure load, i.e. the load at which the oil film breaks up within a load period of 10 seconds.

(2) W.L.: weld load, i.e. the load at which the 4 balls weld together within 10 seconds.

(3) W.S.D.: wear scar diameter in mm, i.e. the average wear diameter at a load of 70 kg and 40 kg respectively in 1 hour.

Catenex 41 (trade name of Shell) was used as base oil.

TABLE 4

| Additive | Conc. in % by weight | ISL (kg) | WL (kg) | WSD (mm) | |
|---|---|---|---|---|---|
| none | — | 60 | 160 | 2.42 | (70 kg) |
| | | | | 1.1 | (40 kg) |
| 1 | 1% | 95 | 235 | 0.77 | (70 kg) |
| 2 | 1% | 110 | 225 | 0.90 | (70 kg) |
| 3 | 1% | — | 190 | 0.80 | (70 kg) |
| 4 | 1% | — | >200 | 0.70 | (70 kg) |
| 5 | 1% | — | 200 | 0.86 | (70 kg) |
| 6 | 1% | — | 180 | 1.1 | (70 kg) |
| 7 | 1% | — | 190 | 0.8 | (70 kg) |
| 8 | 1% | — | 180 | 1.1 | (70 kg) |
| 9 | 1% | — | 180 | 1.0 | (70 kg) |
| 10 | 1% | — | 190 | 0.5 | (40 kg) |
| 11 | 1% | — | 180 | 0.6 | (40 kg) |
| 12 | 1% | — | 180 | 0.3 | (40 kg) |
| 13 | 1% | — | 190 | 0.7 | (70 kg) |
| 14 | 1% | 120 | 205 | 0.61 | (70 kg) |
| 15 | 1% | — | >200 | 0.70 | (70 kg) |
| 16 | 1% | — | 180 | 0.70 | (70 kg) |
| 17 | 1% | — | 180 | 0.50 | (40 kg) |
| 18 | 1% | — | 190 | 0.4 | (40 kg) |
| 19 | 1% | — | 180 | 1.0 | (70 kg) |
| 20 | 1% | — | 180 | 1.3 | (70 kg) |
| 21 | 1% | — | 180 | 1.5 | (70 kg) |
| 24 | 1% | 140 | >270 | 0.3 | (40 kg) |
| 25 | 1% | 110 | >230 | 0.5 | (40 kg) |
| 26 | 1% | — | >200 | 0.5 | (40 kg) |
| 27 | 1% | 110 | >270 | 0.3 | (40 kg) |
| 28 | 1% | 100 | >240 | 0.3 | (40 kg) |
| 29 | 1% | — | >200 | 1.0 | (40 kg) |
| 30 | 1% | — | >200 | 0.5 | (40 kg) |
| 31 | 1% | — | >200 | 0.4 | (40 kg) |
| 32 | 1% | — | 190 | 1.0 | (40 kg) |
| 33 | 1% | 120 | 190 | 0.4 | (40 kg) |
| 34 | 1% | — | 190 | 0.5 | (40 kg) |
| 35 | 1% | — | 190 | 0.5 | (40 kg) |
| 36 | 1% | — | 190 | 0.5 | (40 kg) |
| 37 | 1% | — | 190 | 0.5 | (40 kg) |
| 42 | 1% | 150 | 210 | 0.4 | (40 kg) |

TABLE 4-continued

| Additive | Conc. in % by weight | ISL (kg) | WL (kg) | WSD (mm) | |
|---|---|---|---|---|---|
| 23 | 1% | 100 | 190 | 0.4 | (40 kg) |
| 22 | 1% | — | 190 | 0.4 | (40 kg) |
| 39 | 1% | — | >200 | 0.4 | (40 kg) |
| 40 | 1% | — | >200 | 0.4 | (40 kg) |
| 41 | 1% | — | 190 | 0.4 | (40 kg) |

What is claimed is:

1. A lubricant composition, which comprises a lubricant, which is a mineral oil, synthetic oil or mixture thereof having lubricating properties, and 0.001 to 5 percent by weight, based on the lubricant, of an extreme pressure and antiwear additive of the formula

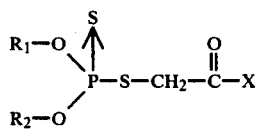

wherein $R_1$ and $R_2$ have the same meaning and each represents alkyl of 3 to 8 carbon atoms, or $R_1$ and $R_2$ together represent alkylene of 2 to 8 carbon atoms, and X represents —OH, —NR$_3$R$_4$ or —OH.NR$_3$R$_4$R$_5$ in which each of $R_3$, $R_4$ and $R_5$ independently represents hydrogen or alkyl of 3 to 18 carbon atoms.

2. A composition according to claim 1 wherein $R_1$ and $R_2$ have the same meaning and each represents alkyl of 3 to 8 carbon atoms, or $R_1$ and $R_2$ together represent alkylene of 2 to 8 carbon atoms, X represents —NR$_3$R$_4$, and $R_3$ and $R_4$ have the same meaning and each represents alkyl of 3 to 18 carbon atoms.

3. A composition according to claim 1 wherein the extreme pressure and anti-wear additive is O,O-diisopropyl-S(N,N-diisopropylcarboxamidomethyl)-dithiophosphate.

4. A composition according to claim 1 wherein the extreme pressure and anti-wear additive is

* * * * *